United States Patent [19]

Harrigan

[11] 4,055,178
[45] Oct. 25, 1977

[54] DRUG DELIVERY DEVICE FOR PREVENTING CONTACT OF UNDISSOLVED DRUG WITH THE STOMACH LINING

[76] Inventor: Roy M. Harrigan, Bromley Mountain Road, Manchester, Vt. 05254

[21] Appl. No.: 665,698

[22] Filed: Mar. 10, 1976

[51] Int. Cl.[2] .................. A61M 31/00; A61J 1/00
[52] U.S. Cl. ................................ 128/260; 128/272
[58] Field of Search ............. 128/260, 272; 119/1, 119/51 R

[56] References Cited

U.S. PATENT DOCUMENTS

| | | | |
|---|---|---|---|
| 2,539,036 | 1/1951 | Schwab | 128/260 |
| 3,415,225 | 10/1968 | Collier | 119/1 |
| 3,548,785 | 12/1970 | Cooper | 119/1 |
| 3,786,813 | 1/1974 | Michaels | 128/260 |
| 3,788,322 | 1/1974 | Michaels | 128/260 |
| 3,844,285 | 10/1974 | Laby | 128/260 |
| 3,901,232 | 8/1975 | Michaels et al. | 128/260 |

FOREIGN PATENT DOCUMENTS

| | | | |
|---|---|---|---|
| 14,140 of | 1893 | United Kingdom | 128/260 |

*Primary Examiner*—Aldrich F. Medbery
*Attorney, Agent, or Firm*—Donald A. Kettlestrings

[57] ABSTRACT

An ingestible drug delivery device is designed so that direct contact by undissolved drug with the stomach lining is avoided.

36 Claims, 33 Drawing Figures

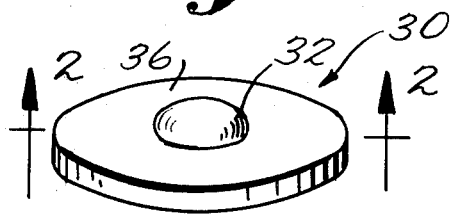
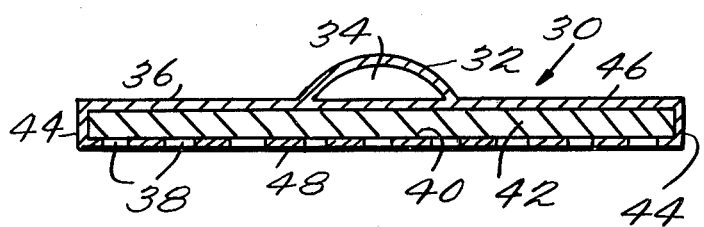
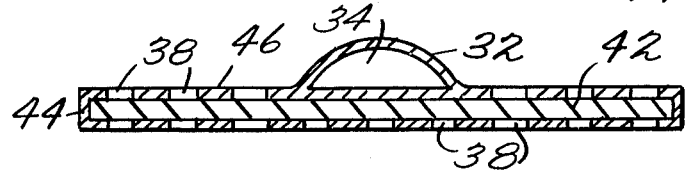
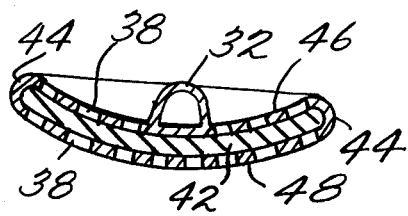
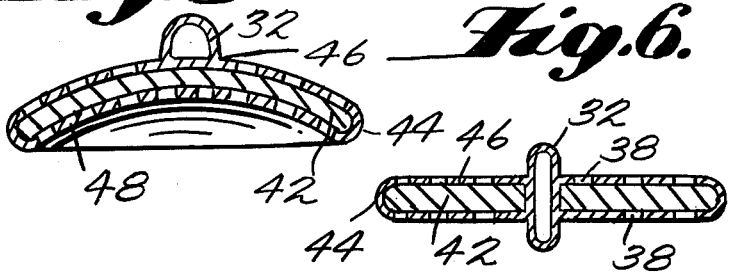
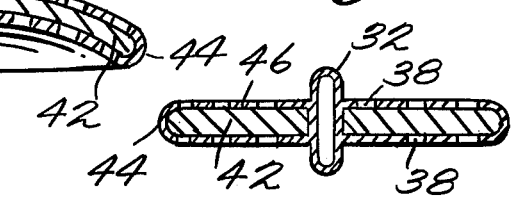
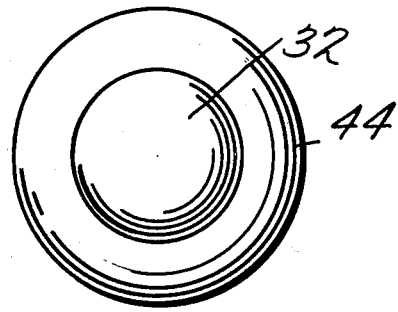
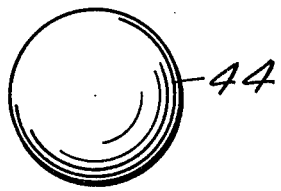
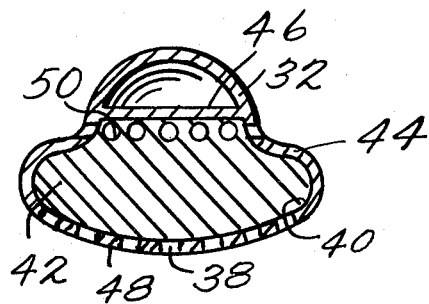
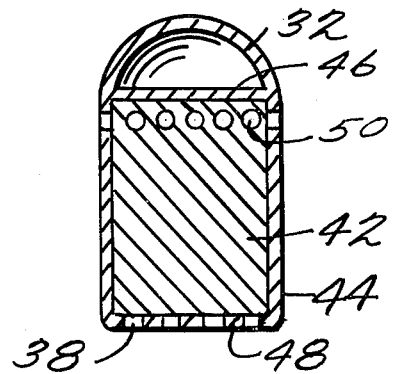

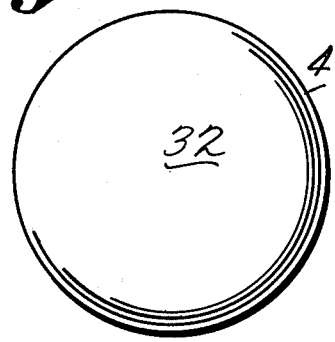
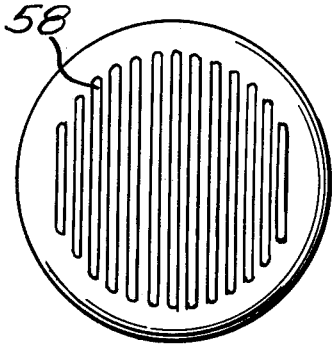
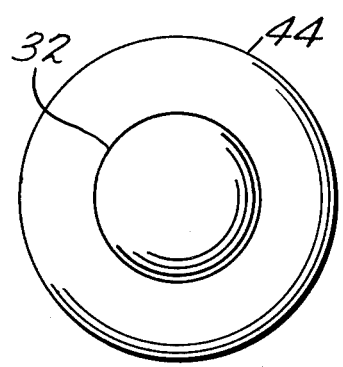
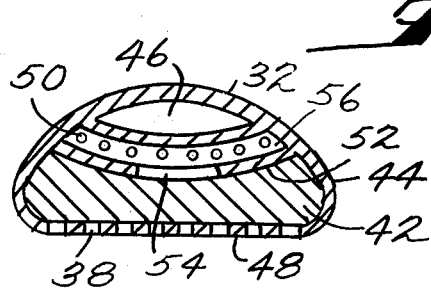
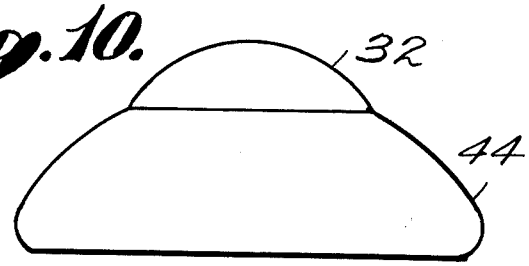
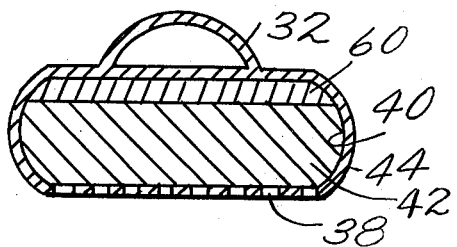
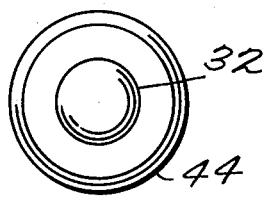
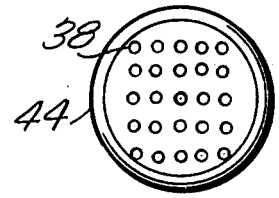
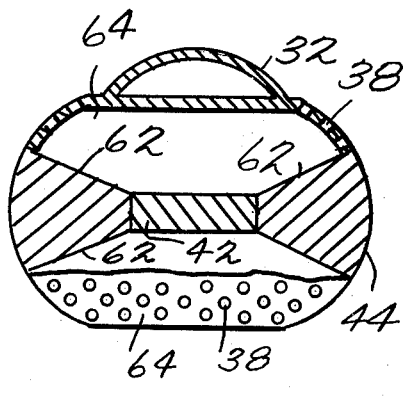
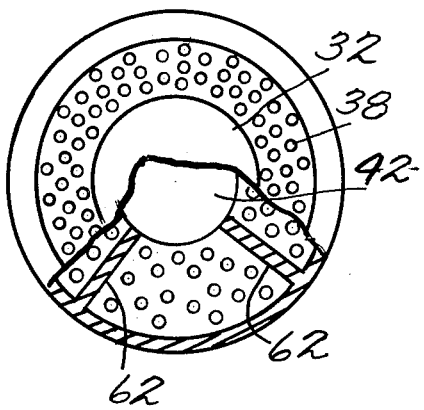
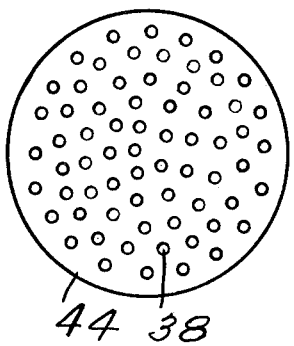

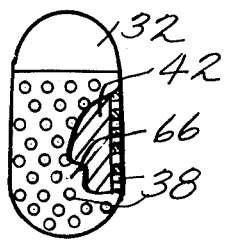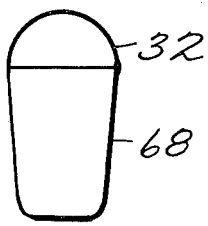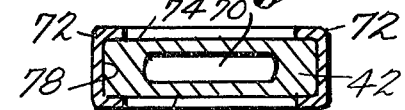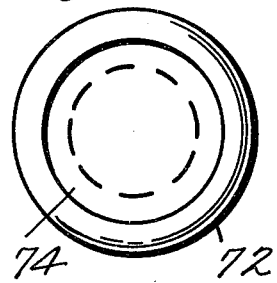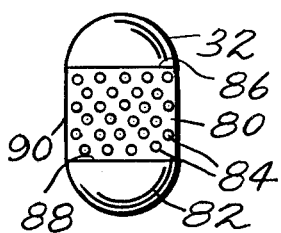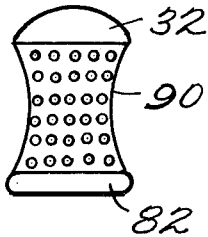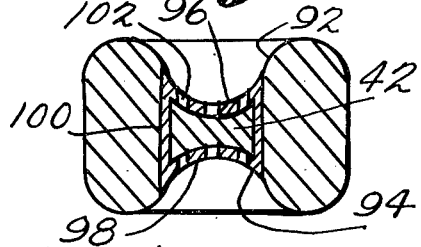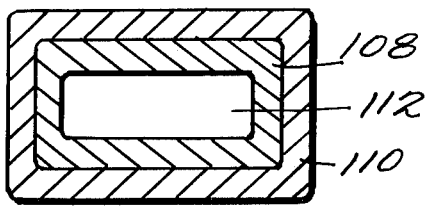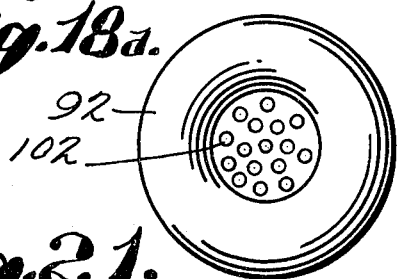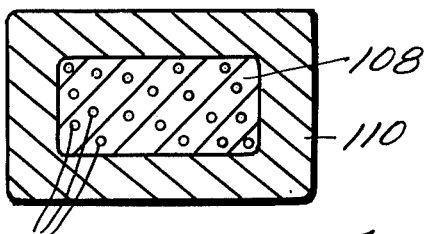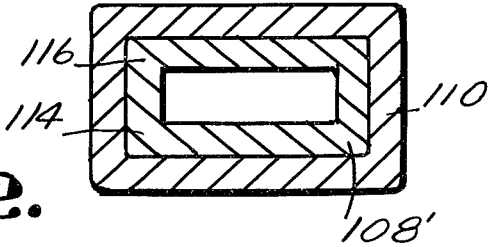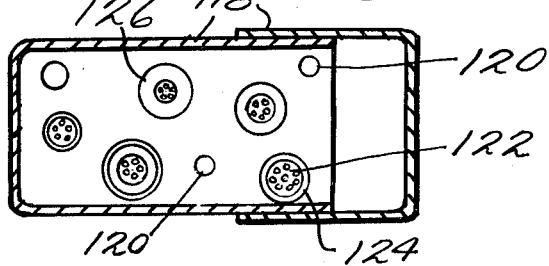

DRUG DELIVERY DEVICE FOR PREVENTING CONTACT OF UNDISSOLVED DRUG WITH THE STOMACH LINING

This invention relates to a drug delivery device, and more particularly to a drug delivery device for enabling the administration of a drug within the stomach without permitting contact of undissolved drug with the stomach lining.

One of the most frequent problems associated with aspirin and many other drugs is that of irritation of the lining of the digestion tract or stomach. This irritation often occurs as a result of the aspirin or other drug contacting the stomach lining prior to dissolution of the drug within the gastric fluids. The aspirin or other drug usually sinks within the gastric fluids to the bottom of the stomach prior to its dissolution, and this direct contact by the drug with the stomach lining can have an undesirable effect. For example, aspirin can cause bleeding of the stomach lining, ulceration, nausea and anemia, and these undesirable effects are magnified in frequency and severity with frequent ingestion of aspirin or other drugs.

Various devices have been developed in order to provide for the delivery of drugs into the body in a controlled manner. U.S. Pat. Nos. 3,788,322 and 3,823,816 describe devices of this general type, but none of the devices yet developed solve the problem addressed and solved by this invention.

It is, therefore, an object of the present invention to provide a drug delivery device for enabling the administration of a drug within the digestive tract without permitting contact of undissolved drug with the digestive tract lining.

Another object is to provide an ingestible drug delivery device that enables a drug or medication to remain in the stomach for a prolonged time period without irritating the stomach lining.

A further object of the invention is the provision of an ingestible drug delivery device provided with flotation means whereby the drug or medication is prevented from contacting the walls of the digestive tract where such contact is detrimental.

Additional objects and advantages of the invention will be set forth in part in the description which follows, and in part will be obvious from the description, or may be learned by practice of the invention. The objects and advantages are realized and attained by means of the instrumentalities and combinations particularly pointed out in the appended claims.

To achieve these and other objects the present invention provides an ingestible drug delivery device for enabling the administration of a drug within the stomach without permitting contact of undissolved drug with the stomach lining. This invention provides means which, as embodied and broadly described, comprise flotation means for enabling the drug delivery device to float in fluids located within the stomach; drug containing means affixed to the flotation means; means in operative relationship with the drug containing means for enabling entry of stomach fluids into the containing means and for enabling exit of the stomach fluids and dissolved drug from the containing means; and means for preventing contact of the undissolved drug with the stomach wall or lining.

Preferably, the flotation means comprises a hollow, enclosed member and a substance, such as air, is located within the hollow member having a specific gravity of a predetermined value to enable the device to float in the gastric fluids.

In accordance with the invention, the drug delivering means comprises a drug container or a shell defining an enabling means that includes a first plurality of apertures providing communication between the interior and the exterior of the shell, and the shell has a drug located therein. Further, the contact-preventing means comprises an aperture-free portion of the shell extending along a peripheral wall thereof whereby any contact by the device with the stomach lining is made by the aperture-free wall.

The present invention relates to a drug delivery device that not only provides for the release of a drug over a prolonged period of time within the stomach but also prevents direct contact of the undissolved drug with the stomach lining. As a result, injury to the stomach lining caused by direct contact of the undissolved drug therewith is avoided. This is a particularly advantageous feature for those persons who are sensitive to certain drugs and also for those persons who are required to use such drugs on a continuing basis. For example, this invention would be extremely advantageous for those persons suffering from arthritis who are required to take large amounts of aspirin on a continuing basis. Frequently these persons complain of stomach and digestive tract disorders as a result of this concentrated ingestion of aspirin, and these disorders can often be traced to aspirin contact with the stomach lining. This invention prevents such direct contact and, therefore, will significantly decrease such problems. Of course, this invention is applicable to the use of many drugs besides aspirin.

It is to be understood that both the foregoing general description and the following detailed description are exemplary and are not restrictive of the invention.

The accompanying drawings, which are incorporated in and constitute a part of this specification, illustrate several embodiments of the invention and, together with the description, serve to explain the principles of the invention.

FIG. 1 is a perspective view of one embodiment of the invention;

FIG. 2 is a section of the device taken on the line 2—2 of FIG. 1 looking in the direction of the arrows;

FIG. 3 shows a section of a further embodiment of the invention;

FIG. 4 is a section of another embodiment of the invention;

FIG. 5 is a cross section of still another embodiment of the invention;

FIG. 6 is a cross sectional view of a further embodiment of the invention;

FIG. 7 is a top plan view of another embodiment;

FIG. 7A is a section of the embodiment shown in FIG. 7;

FIG. 8 is a top plan view of another invention embodiment;

FIG. 8A is a cross sectional view of the embodiment shown in FIG. 8;

FIG. 9 is a top plan view of still another embodiment;

FIG. 9A is a cross section of the embodiment of the invention;

FIG. 10 is an elevation view of a further embodiment of the invention;

FIG. 10A is a bottom plan view of the embodiment shown in FIG. 10;

FIG. 10B is a top plan view of the embodiment shown in FIG. 10;

FIG. 11 is a top plan view of another embodiment of the invention;

FIG. 11A is a bottom plan view of the embodiment shown in FIG. 11;

FIG. 11B is a section of the embodiment shown in FIG. 11;

FIG. 12 is a top plan view of still another invention embodiment;

FIG. 12A is a bottom plan view of the embodiment shown in FIG. 12;

FIG. 12B is a section of the FIG. 12 embodiment;

FIG. 13 is a perspective view of another embodiment of the invention;

FIG. 14 is a perspective view of another invention embodiment;

FIG. 15 is a top plan view of another embodiment;

FIG. 15A is a section of the FIG. 15 embodiment;

FIG. 16 is a perspective view of a further embodiment of the invention;

FIG. 17 is a perspective view of still another invention embodiment;

FIG. 18 is a section view of a further embodiment of the invention;

FIG. 18A is a top plan view of the embodiment shown in FIG. 18;

FIG. 19 is a section view of another invention embodiment;

FIG. 20 is a section view of a further embodiment of the invention;

FIG. 21 is a section of an additional invention embodiment; and

FIG. 22 is a diagrammatic section view of still another embodiment of this invention.

With reference now to the drawings, wherein like reference numerals designate like or corresponding parts throughout the several views, and which drawings are examples of various embodiments of the invention that are not to be construed as limiting, one embodiment of the invention is illustrated in FIGS. 1 and 2. The ingestible drug delivery device is generally indicated by numeral 30, and comprises flotation means defining a hollow, enclosed member 32. A cavity or chamber 34 is formed by member 32, and a substance is located within the cavity having a specific gravity of a predetermined value to enable the drug delivery device to float in the fluids located within the stomach. The substance located within cavity 34 may include air, air under partial vacuum, or any other suitable gas, liquid or solid having the desired specific gravity and which gas, liquid or solid is harmless when released to the interior of the gastro-intestinal tract.

Also associated with the device are drug delivering means comprising a container or shell 36 defining a first plurality of apertures 38 providing communication between the interior 40 of shell 36 and the exterior of the shell. Located within the shell interior is a drug or medicament 42.

An important feature of this invention permits drug 42 to be completely dissolved within the gastric fluids or permits only harmless small particles of drug to be released into the stomach fluids before any of the drug is permitted to contact the stomach lining. This is accomplished partially by flotation member 32 which causes the drug delivery device to remain floating within the gastric fluids until drug 42 is dissolved or dispersed from interior 40 of the device. Direct contact by undissolved drug with the stomach lining is also prevented by means affixed to a part of shell 36.

This contact-preventing means comprises an aperture-free portion 44 of shell 36 extending along a peripheral wall thereof whereby any contact by the drug delivery device with the stomach lining is made by this aperture-free portion 44 of the shell. More specifically, the device of this invention includes a top wall 46, a bottom wall 48 and aperture-free portion 44 of the shell defines a peripheral wall extending between top wall 46 and bottom wall 48.

Although not specifically illustrated in the drawings, apertures 38 may be covered by a water-soluble film. This film acts to seal the apertures and to prevent escape of the drug prior to its ingestion into the stomach. The film will then dissolve in the stomach fluids to permit movement of the drug from the interior of the device into the stomach fluids.

The size of apertures 38 may also vary to a considerable extent as determined by the solubility and physical configuration of the drug. If the drug is readily soluble, the size of the apertures can be smaller than if the drug is not so readily soluble in the stomach fluids. In some cases, the drug may be such that it can pass through a permeable membrane positioned across apertures 38, such as by osmosis.

Although aspirin is contemplated as a drug particularly adaptable for use with this invention, it should be understood that many drugs can be administered with the delivery device of this invention. Particularly effective is the use of a carbonate located with the drug to facilitate movement of the drug through apertures 38 and to facilitate ultimate rapid dissolution of the drug in the stomach fluids. It has also been found that the usual excipients and binders used in conventional tablets may be desirably dispensed with to facilitate the desired action and movement of the drug through the apertures. In addition, if powdered aspirin is used, wetting or emulsifying agents may be combined with the powdered aspirin to facilitate its rapid dissolution.

The drug delivery device described is of a swallowable size, and it remains afloat within the stomach long enough for drug 42 to pass into the stomach through apertures 38. The device remains afloat until all of the drug is dissolved through apertures 38, and peripheral wall 44 prevents direct contact of the undissolved drug with the stomach wall. Because the device continues to float during the process of dissolution of the drug, contact by the undissolved drug or by large particles thereof is prevented. After the drug has been totally dissolved, the material of shell 36 and of member 32 may also be dissolved in the stomach or in the intestinal tract, or the material may be passed through the intestinal tract and ultimately eliminated.

Alternative embodiments of the invention are illustrated in FIGS. 3–6 wherein additional apertures 38 are also located along top wall 46 of the shell. Flotation member 32 can be positioned above shell 46, as in the embodiments of FIGS. 1–5, or flotation member 32 may extend throughout the thickness of the drug delivery device, as illustrated in FIG. 6.

In order to increase the area of contact between apertures 38 and the fluids within the stomach, shell 46 can be shaped as shown in FIGS. 4 and 5. Specifically, FIG. 4 illustrates an embodiment of the device wherein top wall 46 is concave in exterior appearance and wherein bottom wall 48 is convex in exterior appearance. Conversely, top wall 46 may be formed as to be convex in exterior appearance while bottom wall 48 is concave in exterior appearance, as shown in FIG. 5.

In each of the embodiments shown in FIGS. 3-6, peripheral wall 44 is provided to prevent direct contact of undissolved drug with the stomach wall. As the device floats within the fluids of the stomach, and even if it moves to a position adjacent to the stomach wall, peripheral wall 44 will contact the stomach lining so that no direct contact of drug 42 with the stomach lining occurs. The addition of apertures 38 in top wall 46 increases the rate at which the drug is dissolved into the stomach fluids and facilitates movement of the fluids through the interior of the device to flush the drug out.

Another embodiment of the invention is illustrated in FIGS. 7 and 7A wherein top wall 46 is substantially completely covered by flotation member 32. The device is generally cylindrical in shape, but peripheral wall 44 is substantially s-shaped and a second plurality of apertures 50 are located at the uppermost portion of peripheral wall 44. Apertures 50 may be substantially the same size as apertures 38, located in bottom wall 48, but preferably, apertures 50 are larger than apertures 38 to facilitate the entry of water or stomach fluids into the interior 40 of the device. Drug 42 is mixed with and dissolved in the fluids.

The fluids then cause the drug to pass outwardly from the interior of the device through apertures 38 and into the stomach where further dissolution of the drug occurs. Because of the size of apertures 38 and 50, however, release of large particles of the drug into the stomach is avoided and direct contact of such undissolved particles of drug with the stomach lining is also avoided. As in the preceding embodiments, this embodiment of the device is provided with peripheral wall 44 which contacts the stomach lining and avoids direct contact of undissolved drug therewith.

A further embodiment of the invention is illustrated in FIGS. 8 and 8A wherein the device is substantially cylindrical in shape and wherein flotation member 32 substantially covers top wall 46. Apertures 50 are located at the uppermost portion of peripheral wall 44, and these apertures are also preferably larger than apertures 38 located in bottom wall 48.

A modified embodiment of the invention is illustrated in FIGS. 9 and 9A wherein a spacer wall 52 extends inwardly from peripheral wall 44 and is positioned below apertures 50. At least one large aperture 54 is located within spacer 52 and drug 42 is located between spacer wall 52 and lower wall 48.

The spacer wall together with top wall 46 and peripheral wall 44 defines an upper cavity 56, and apertures 50 enable water or stomach fluid to directly enter into cavity 56 and then to pass downwardly through larger aperture 54 into contact with the drug. Thus, when the device is first positioned within the stomach, a quick inrushing of fluids through apertures 50 into cavity 56 occurs so that these fluids are quickly passed through aperture 54 to mix with drug 42. This facilitates the quick dissolution of the drug and enables the drug to quickly pass outwardly through apertures 38 into the surrounding stomach fluids.

FIGS. 10, 10A and 10B illustrate still a further embodiment of the invention, and one substantially similar to that illustrated in FIGS. 1 and 2 with the exception that slits 58, instead of circular apertures 38, are used to substantially increase the area of contact between the drug and the stomach fluids. This increase in contact area has the effect of substantially decreasing the time required for dissolution of the drug.

FIGS. 11, 11A and 11B illustrate still another embodiment of the invention wherein a gas producing layer 60 is positioned within the interior 40 of the device and in close proximity to drug 42 whereby reaction of water or stomach fluids with the gas producing layer 60 causes effervescence to occur and ultimately results in quick dispersion of drug 42 through holes 38 and into the stomach fluids. Alternatively, the gas producing material 60 may be dispersed throughout drug 42 to enhance the effervescent action.

A further embodiment of this invention is illustrated in FIGS. 12, 12A and 12B wherein drug 42 is held within the interior of the device by means of supports 62 whereby portions 64 of the interior are vacant. These vacant volumes 64 permit expansion of drug 42 into areas 64 or permit rapid ingress of water or stomach fluids through apertures 38 and into the interior of the device for effective mixing with the drug. These additional volumes 64 within the interior of the device enable drug 42 to be more completely dissolved within the water or stomach fluids prior to the time that the dissolved drug exits through apertures 38 into the surrounding stomach fluids. This, of course, substantially decreases the possibility that large particles of undissolved drug will be permitted to escape to the surrounding fluids and that direct contact by such undissolved drug with the stomach lining will occur.

Still another invention embodiment is illustrated in FIG. 13 wherein flotable member 32 is affixed to and above a substantially cylindrically shaped bottom portion 66. Bottom portion 66 defines a plurality of apertures 38 throughout its entire surface, and drug 42 is located within bottom portion 66 and below flotation member 32. This embodiment is particulary effective for quickly distributing the drug into the surrounding stomach fluids when the drug is combined with an effervescent. The device remains afloat within the stomach fluids, and the large number of apertures 38 enables the quick dissolution of the drug and avoids direct contact of undissolved drug with the bottom of the stomach. Further, because of the action of the effervescent and the quick dispersion of the drug through apertures 38, only very slight contact by the drug with the sides of the stomach lining is possible and prolonged contact of any undissolved drug with the stomach lining is completely avoided.

A further embodiment of the invention is illustrated in FIG. 14 wherein flotation member 32 is comprised of a material that will dissolve in gastric fluids within a first predetermined time period. Drug delivering means 68 is affixed to flotation member 32, and includes a hollow, enclosed, walled member comprised of a material that will dissolve in gastric fluids within a second predetermined time period of a shorter duration than the first time period. Drug 42 is located within delivering member 68 to be released into the stomach when delivering member 68 dissolves in the gastric fluids. This embodiment is particularly useful for dispersing a liquid suspension of medication into the stomach. For example, drug 42 may be comprised of a drug or medication suspended in a liquid carrier, or the medication itself may be in liquid form. Upon entry of the device into the stomach, the device remains floating within the stomach fluids while drug delivery member 68 dissolves. This dissolution of member 68 enables the medication to be released into the stomach fluids. Flotation member 32 may then completely dissolve in the stomach fluids after the medication has been released, or the flotation member may be permitted to enter the intestinal tract where it can be dissolved or ultimately eliminated. This embodiment of the invention prevents direct contact by the liquid medication with the esophagus or with the stomach walls prior to its mixture with the stomach fluids.

A further embodiment of the present invention is illustrated in FIGS. 15 and 15A wherein a drug composition 42 is compressed to form an article of predetermined shape, and wherein an interior cavity 70 is defined within the compressed drug. The interior of cavity 70 is filled with a substance that enables the device to float in the stomach fluids, and a shielding material 72 covers a predetermined portion of compressed drug 42 for preventing contact of undissolved drug with the stomach lining while the device is floating in the stomach fluids. Drug 42 may be held together by a conventional binder substance, and the compressed drug is preferably formed in the shape of a cylinder having a top surface 74, a bottom surface 76 and a side surface 78 extending between the top and bottom surfaces. Shielding material 72 is preferably affixed to and covers side surface 78, and the shielding material may further be extended to cover a predetermined portion of the top and bottom surfaces. Shielding material 72 may be comprised of any of a number of well known materials, and one such inexpensive material, for example, could be beeswax. The material 72 may be such that it dissolves in the stomach fluids after the drug has been dissolved or the material may pass through the intestinal tract to be dissolved or eliminated.

Although the present invention contemplates the use of flotation means to enable the drug delivery device to float in the stomach fluids while the drug is being dispersed therein, the invention also contemplates the use of a drug delivery device that does not float but which prevents direct contact of undissolved drug with the stomach lining. One such embodiment of this invention is illustrated in FIG. 16 wherein a flotation means or member 32 is affixed to drug delivery means or member 80, and wherein weighted means or member 82 is affixed to drug delivery member 80 for enabling the device to sink in the stomach fluids. The combined effect of flotation member 32 and weighted member 82 causes the device to ultimately come to rest on the lowest part of the stomach with weighted member 82 resting on the stomach floor. Flotable member 32 is comprised of a hollow, enclosed member having a substance located therein with a specific gravity of a predetermined value to enable the flotation member to float within the gastric fluids. Delivery member 80 comprises a substantially cylindrical shell defining a plurality of apertures 84 providing communication between the interior and the exterior of the shell, and a drug or medication is located within delivery member or shell 80.

Shell 80 defines a top wall 86, a bottom wall 88 and a peripheral wall 90 extending between the top and bottom walls, and apertures 84 are positioned along the peripheral wall. Flotation member 32 is affixed to top wall 86 and weighted member 82 is affixed to bottom wall 88.

As the device illustrated in FIG. 16 settles to the bottom of the stomach and ultimately is positioned with weighted end 82 down on the stomach floor, the stomach fluids enter through apertures 84 and into the interior of the device where the drug is dissolved and allowed to exit through apertures 84 into the surrounding stomach fluids. Thus, although the device itself is positioned on the stomach floor, no undissolved drug or large chunks thereof are permitted to come into direct contact with the stomach lining.

Another embodiment of the invention is illustrated in FIG. 17, and this embodiment is identical to that illustrated in FIG. 16 with the exception that peripheral wall 90 is concave in exterior appearance so that any possibility of direct contact by undissolved drug with the stomach lining or with the side wall of the stomach is avoided.

A further embodiment of this invention is illustrated in FIGS. 18 and 18A wherein a shell 92, substantially in the shape of a toroid, is provided and wherein the shell defines a central bridge portion 94. This bridge defines a top wall 96, a bottom wall 98 and a peripheral wall 100, extending between the top and bottom walls, and a plurality of apertures 102 are positioned along top and bottom walls 96 and 98. Drug 42 is located within bridge portion 94, and water or stomach fluids enter through apertures 102 to dissolve the drug and to enable the dissolved drug to exit through those same apertures into the surrounding stomach fluids.

The toroidal shape of shell 92 enables the device to rest on the stomach floor without danger of direct contact of undissolved drug or large chunks thereof with the stomach lining. After the drug has been dissolved and has entered into the surrounding stomach fluids, the material of shell 92 is such that it may either by dissolved within the stomach fluids or may be permitted to enter the intestinal tract for dissolution there or ultimate elimination.

An alternative configuration for the toroidally shaped device (not illustrated) provides for shell 92 being filled with drug 42 and apertures 102 being located along the entire extent of curved walls 104 and 106 defining a central bridge portion of the toroid.

Although this invention has been described with emphasis on the use of aspirin or aspirin compounds as the drug to be administered, it should be understood that this invention is applicable to many drugs, and it is particularly applicable to the use of various drugs with an effervescent. The usual excipients and binders used in tablets may be dispensed with in this invention to facilitate the desired action and ready dissolution of the drug within the stomach fluids. If a powdered drug, such as aspirin, is used it may be desirable to use a wetting agent in combination therewith to increase the facility for dissolution in the stomach fluids. Bufferin is another drug which is particularly adapted for use with this invention, and the use of aspirin with a carbonate, such as $MgCO_3$, has also been found to be very effective. The action of the carbonate in combination with the normal stomach acids found in the stomach fluids causes small bubbles to attach to the undissolved drug particles so as to keep them in suspension until the drug is totally dissolved. This is a particularly desirable action, and prevents direct contact of undissolved drug with the stomach lining.

The device of this invention is also particularly useful for delivering antacids into the stomach fluids, and enables the antacids to remain in the stomach for a longer period of time. This, of course, enables the antacid to work completely to its maximum ability to neutralize the stomach acid.

The use of antacids is even more effective if the antacid dissolves gradually during a time period or if the antacid is positioned within time release binders, and the acidity of the stomach can be further controlled by providing that such antacids and/or antacid binders dissolve only in stomach fluids of a predetermined acidity.

One embodiment of this invention specifically designed for the introduction of antacids into the stomach is illustrated in FIG. 19. In this embodiment, first drug means 108 is provided for dissolution only in a fluid having a pH value within a predetermined range. Second drug means 110 is affixed to first drug means 108 for dissolution in stomach fluids. Flotation means 112 is provided in operative relationship with first drug means 108 for enabling the device to float in the stomach fluids.

More specifically, the first and second drug means preferably include an antacid material, and first drug means 108 is a tightly compacted antacid, such as $CaCO_3$, that will dissolve only in stomach fluids of a predetermined acidic pH range. Second drug means 110 is preferably an antacid medicament compacted more loosely than first drug means 108 so that drug layer 110 will dissolve in the stomach fluids in the manner of a normal antacid tablet.

Flotation means 112 preferably comprises an interior cavity having a substance located therein. The specific gravity of the substance located within the cavity is of a predetermined value to enable the device to float in the fluids of the stomach.

An alternative embodiment is illustrated in FIG. 20 wherein the flotation means includes a plurality of cavities 112' located within first drug means 108, and wherein each of the cavities contains a substance having a specific gravity of a predetermined value to enable the device to float in the fluids located within the stomach.

Another related embodiment of this invention is illustrated in FIG. 21 wherein first drug means 108' includes a medicament 114 and binder 116 holding the medicament together. Binder 116 is preferably comprised of a material that dissolves only in a fluid having an acidic pH within a predetermined range. In addition, binder material 116 is preferably comprised of a material that dissolves at a predetermined rate to provide a continuous release of medicament 114 into the stomach over a predetermined time period.

Thus, when the acidity of the stomach is within a predetermined pH range, outer medicament layer 110 will quickly dissolve within the stomach fluids after the device has been ingested, but interior medicament layers 108, 108' will only dissolve if the acidity of the stomach is above a predetermined level, and then at a predetermined rate. This assures that the antacid will be dissolved only when needed. Furthermore, this gradual and controlled release of antacid prevents so-called "acid rebound" where the sudden introduction of antacid material into an acid stomach fluid can ultimately result in the stomach fluid becoming even more acidic. The flotation feature of these invention embodiments also permits the antacid to remain in the stomach for a longer period of time and enables the gradual and controlled release of the antacid into the stomach only as needed. This has the additional desired effect of reducing the amount of antacid required to neutralize an acid stomach.

A further embodiment of the invention is illustrated in FIG. 22 wherein a hollow, enclosed capsule 118 encases a first plurality 120 of flotable medicament particles. A second plurality 122 of flotable medicament particles are also positioned within the capsule 118, and a first material 124 covers and is affixed to each of the second plurality of particles 122. Material 124 is substantially totally dissolvable during a first predetermined time period in a fluid having an acidic pH within a predetermined range.

A third plurality of flotable medicament particles 126 are also positioned within capsule 118, and a second material 128 covers and is affixed to each of the particles 126. Second material 128 is characterized by being substantially totally dissolvable during a second predetermined time period in a fluid having an acidic pH within a predetermined range. Of course, any number of additional coated particles having varied dissolution times may be provided in order to vary the total amount of medicament released into the stomach fluids during predetermined time periods.

Particles 120, 122 and 126 are all preferably flotable in the stomach fluids. For example, each of the particles 120, 122 and 126 may define at least one enclosed cavity, and a substance may be located within each of the cavities having a specific gravity of a predetermined value to enable each of the particles to float in the fluids located within the stomach. Alternatively, if the specific gravity of each of the particles is of a value to enable the particles to float in the stomach fluids without the use of such cavities, the cavities may be eliminated.

Thus, the embodiment of this invention illustrated in FIG. 22 enables antacid particles to be floated within the stomach fluids and to release the antacid medicament into the stomach fluids in a controlled manner over a predetermined time period. The additional feature of this invention providing for materials 124 and 128 that are dissolvable only in fluids of a predetermined acidic pH enable these medicament particles to remain floating within the stomach fluids and to be released into the stomach fluids only when the acidity of the stomach fluids reaches a predetermined value. Accordingly, the antacid medicament is permitted to remain in the stomach for a longer period of time, "acid rebound" is avoided and the amount of antacid necessary may be reduced in view of the prolonged release thereof into the stomach fluids. The controlled release of antacid in the manner provided for by the embodiments illustrated in FIGS. 19–22 also prevents or reduces the side effects common to the use of antacids.

Of course, the embodiments of FIGS. 19–21 are applicable for use with medicaments other than antacids and are particularly adaptable for use with any drug not harmful to the wall of the stomach upon direct contact.

The size of the apertures in the devices of this invention may vary depending upon the medication used, the time desired for dissolution of the drug and the concentration and solubility of the drug located within the device. However, apertures having a diameter of substantially 0.010 to 0.050 inch, for example, may be used, but it should be understood that apertures of different sizes may also be used. The more readily soluble the drug and other chemicals located with the drug, the smaller may be the aperture sizes. In fact, the aperture sizes may be decreased to the point that a drug escapes from the interior of the device to the surrounding stomach fluids by means of diffusion through a permeable membrane or osmosis.

It may also be desirable to combine an acid powder, such as citric acid, with aspirin and a gas producer such as $NaHCO_3$ or $CaCO_3$. The addition of such an acid power to the medication located within the devices of this invention enables the simple addition of moisture to cause the necessary effervescence and quick dissolution of the drug. Without the acid powder, the acid within the stomach fluids is required to react to form the gas, and the stomach acid may be quickly neutralized so that the effervescent action ceases. The addition of acid powder avoids this possibility and ensures that effervescence will always occur sufficiently to completely disperse and dissolve the aspirin or other drug.

In each of the embodiments of the invention, it is preferable that the thickness of the shell or wall immediately adjacent to the apertures be as thin as possible to readily enable the stomach fluids to enter into the interior of the device for dissolution of the drug positioned therein. Of course, where effervescent or carbonation materials are also located with the drug in the interior of the device, the walls of the device will have to be thicker and stronger to oppose the gas pressure created upon the occurrence of effervescence within the device.

The present invention, thus provides a unique and novel drug delivery device that permits the drug to remain within the stomach over a prolonged period while also preventing direct contact of the undissolved drug or large particles thereof with the stomach lining. Many drugs, such as aspirin and phenylbutazone, as examples, can irritate the stomach lining and can cause such serious side effects as ulcers, bleeding of the stomach wall, anemia and nausea when the drug comes into direct contact with the stomach lining. The drug delivery device of this invention enables these drugs to be safely ingested without danger of direct contact with the stomach lining, and these dangerous side effects are completely avoided.

The invention in its broader aspects is not limited to the specific details shown and described, and departures may be made from such details without departing from the principals of the invention and without sacrificing its chief advantages.

What is claimed is:

1. A drug delivery device for use in body cavities containing fluid, said device comprising:
   means for containing a drug;
   a drug located within said containing means;
   means in operative relationship with said drug containing means for enabling entry of said fluid into said containing means and into dissolving contact with said drug and for enabling exit of said fluid and said dissolved drug from said containing means;
   said enabling means being located in the device to substantially prevent physical contact of said drug in undissolved form with the body cavity walls.

2. A drug delivery device as in claim 1 further including flotation means in operative relationship with said drug containing means for enabling said device to float in said fluid.

3. A drug delivery device as in claim 2 wherein said flotation means comprises a hollow, enclosed member and a substance located within said member having a specific gravity of a predetermined value to enable said device to float in the fluids located within a body cavity, such as the stomach.

4. A drug delivery device as in claim 3 wherein said drug containing means comprises a shell defining said enabling means, said enabling means including a first plurality of apertures providing communication between the interior and the exterior of the shell.

5. A drug delivery device as in claim 4 wherein an aperture-free portion of said shell extends along a peripheral wall of said containing means whereby any contact by said device with the stomach or other body cavity lining is made by said aperture-free wall.

6. A drug delivery device as in claim 5 wherein said shell defines a top wall and a bottom wall, said peripheral wall extending between said top and bottom walls, and wherein said apertures are positioned along the lower wall of said shell.

7. A drug delivery device as in claim 6 wherein said hollow, enclosed member is affixed above said shell.

8. A drug delivery device as in claim 6 wherein said apertures are also positioned along the top wall of said shell.

9. A drug delivery device as in claim 6 wherein said top wall of said shell is concave in exterior appearance and wherein said bottom wall is convex in exterior appearance.

10. A drug delivery device as in claim 6 wherein said top wall is convex in exterior appearance and wherein said bottom wall is concave in exterior appearance.

11. A drug delivery device as in claim 6 wherein said shell is substantially cylindrical in shape.

12. A drug delivery device as in claim 6 further including a second plurality of apertures located at the uppermost portion of said peripheral wall.

13. A drug delivery device as in claim 12 wherein each of said second plurality of apertures is larger than each of said first plurality of apertures.

14. A drug delivery device as in claim 13 wherein said top wall is completely covered by said flotation means.

15. A drug delivery device as in claim 14 wherein said bottom wall is thinner than said side wall.

16. A drug delivery device as in claim 15 further including a spacer wall extending inwardly from said peripheral wall and positioned below said second plurality of apertures, said spacer wall defining at least one aperture therein, and said drug located between said spacer wall, said lower wall and said peripheral wall.

17. A drug delivery device as in claim 12 wherein said peripheral wall is substantially s-shaped.

18. A drug delivery device as in claim 17 wherein each of said second plurality of apertures is larger than each of said first plurality of apertures.

19. A drug delivery device as in claim 18 wherein said top wall is completely covered by said floatation means.

20. A drug delivery device as in claim 19 wherein said bottom wall is thinner than said side wall.

21. A drug delivery device as in claim 5 wherein the drug located within the shell includes a substance which effervesces in the presence of fluids located within the stomach.

22. An ingestible drug delivery device for enabling the administration of a drug within the stomach including means for preventing contact of undissolved drug with the stomach lining, said device further including:
   said drug forming an article of predetermined shape, and defining an interior cavity;
   a substance located within said cavity having a specific gravity of a predetermined value to enable said device to float in the fluid located within the stomach; and wherein said contact preventing means includes
   a shielding material covering a predetermined portion of said drug for preventing contact of said undissolved drug with the stomach lining.

23. A drug delivery device as in claim 22 wherein said composition is held together by a binder substance.

24. A drug delivery device as in claim 22 wherein said composition is in the shape of a cylinder having a top surface, a bottom surface and a side surface extending between said top and bottom surfaces; said shielding material affixed to and covering said side surface.

25. A drug delivery device as in claim 24 wherein said shielding material further is affixed to and covers a predetermined portion of each of said top and bottom surfaces.

26. A drug delivery device as in claim 25 wherein said shielding material comprises beeswax.

27. An ingestible drug delivery device for enabling the administration of a drug within the stomach without permitting contact of undissolved drug with the stomach lining, said device comprising: flotation means for enabling said device to float in fluids located within the stomach, said flotation means including a hollow, enclosed, walled member comprised of a material that will dissolve in gastric fluid within a first predetermined time period;

drug delivering means affixed to said flotation means, said delivering means including a hollow, enclosed, walled member comprised of a material that will dissolve in gastric fluid within a second predetermined time period; that is shorter than first time period and a drug located within said delivering means to be released into the the stomach when said delivering means dissolves in the gastric fluid.

28. A device as in claim 27 wherein said drug is a liquid suspension of medication.

29. An ingestible drug delivery device for enabling the administration of a drug within the stomach without permitting contact of undissolved drug with the stomach lining, said device comprising:

flotation means for floating in the fluids located within the stomach;

drug delivering means affixed to said flotation means for delivering a drug into the fluids of the stomach; and weighted means affixed to said drug delivering means for enabling said device to sink in the fluids of the stomach and for acting in concert with said flotation means to enable said device to ultimately come to rest on the floor of the stomach in a predetermined orientation after having been ingested.

30. A drug delivery device as in claim 29 wherein said flotation means comprises a hollow, enclosed member and a substance located within said member having a specific gravity of a predetermined value to enable said device to float in gastric fluids.

31. A drug delivery device as in claim 30 wherein said drug delivering means comprises a substantially cylindrical shell defining a plurality of apertures providing communication between the interior and the exterior of the shell, and a drug located within the shell.

32. A drug delivery device as in claim 31 wherein said shell defines a top wall, a bottom wall, and a peripheral wall extending between said top and bottom walls and wherein said aperatures are positioned along said peripheral wall.

33. A drug delivery device as in claim 32 wherein said top wall is affixed to said flotation means and wherein said bottom wall is affixed to said weighted means.

34. A drug delivery device as in claim 33 wherein said peripheral wall is concave in exterior appearance.

35. An ingestible drug delivery device for enabling the administration of a drug within the stomach without permitting contact of undissolved drug with the stomach lining, said device comprising:

a shell substantially in the shape of a toroid and defining a central, bridge portion;

said bridge portion further defining a plurality of apertures providing communication between the interior and the exterior of said shell, and a drug located within the bridge portion of said shell.

36. A drug delivery device as in claim 35 wherein said bridge portion defines a top wall, a bottom wall and a peripheral wall extending between said top and bottom walls and wherein said apertures are positioned along said top and bottom walls.

* * * * *

UNITED STATES PATENT AND TRADEMARK OFFICE
CERTIFICATE OF CORRECTION

PATENT NO. : 4,055,178
DATED : October 25, 1977
INVENTOR(S) : Roy M. Harrigan

It is certified that error appears in the above–identified patent and that said Letters Patent are hereby corrected as shown below:

In Claim 27, line 14, delete the semicolon ";" and insert --said--between "than" and "first". Line 15, insert a semicolon --;-- between "period" and "and".

Signed and Sealed this

Seventh Day of February 1978

[SEAL]

Attest:

RUTH C. MASON
Attesting Officer

LUTRELLE F. PARKER
Acting Commissioner of Patents and Trademarks